United States Patent [19]

Condouris et al.

[11] 4,298,608

[45] * Nov. 3, 1981

[54] METHOD FOR BLOCKING HIGH FREQUENCY NERVE STIMULATION

[75] Inventors: George A. Condouris, Glen Ridge, N.J.; John Yelnosky, Warrington, Pa.; Richard L. Riley, North Wales, Pa.; Chong M. Won, Warrington, Pa.; George H. Douglas, Malvern, Pa.; William L. Studt, Harleysville, Pa.

[73] Assignee: William H. Rorer, Inc., Fort Washington, Pa.

[*] Notice: The portion of the term of this patent subsequent to Apr. 15, 1997, has been disclaimed.

[21] Appl. No.: 139,484

[22] Filed: Apr. 11, 1980

Related U.S. Application Data

[63] Continuation of Ser. No. 959,858, Nov. 13, 1978, Pat. No. 4,198,408.

[51] Int. Cl.$^3$ .............................................. A61K 31/53
[52] U.S. Cl. .................................................... 424/249
[58] Field of Search ........................ 424/249; 544/211

[56] References Cited

U.S. PATENT DOCUMENTS 3,983,116  9/1976  Lin ...................................... 544/211
4,198,408  4/1980  Condouris ........................... 424/249

Primary Examiner—Sam Rosen
Attorney, Agent, or Firm—James A. Nicholson; Alexis Barron

[57] ABSTRACT

1,4-Disubstituted-1,2-dihydro-1,3,5-triazin-2-ones are used to block conduction of high frequency nerve impulses by selectively acting to substantially completely block high frequency impulses without significantly blocking conduction of a single impulse. The effect is reversible when the drug is withdrawn.

4 Claims, No Drawings

METHOD FOR BLOCKING HIGH FREQUENCY NERVE STIMULATION

This is a continuation of application Ser. No. 959,858, filed Nov. 13, 1978, now U.S. Pat. No. 4,198,408.

BACKGROUND OF THE INVENTION

The mode of action of clinically useful local anesthetic agents is generally believed to be on the nerve membrane. Local anesthetic agents can produce several effects on nerve membranes which lead to blocking the propagation of nerve impulses. There are numerous therapeutic agents known which produce a local anesthetic effect in mammalian systems. Generally, these therapeutic agents are categorized in two categories: (a) those which exert their local anesthetic effect by acting at receptive sites within the nerve membrane to block the sodium channels and for those which do not penetrate the membrane easily, by acting on exterior sites to block the exterior openings of the sodium; and (b) those which act through a less selective process on the membrane by exerting a physicochemical effect or a combination of effects on the nerve cell.

Tetrodotoxin, which is one of the most potent blockers of axonal conduction, is an example of a local anesthetic agent generally considered to act by blocking the exterior openings of the sodium channels. Procaine and licocaine exemplify local anesthetic agents which are believed to exert their effect by penetrating into the membrane and acting at sites deeper within the sodium channels. It is generally believed that both categories of drugs act by impairing by function of sodium transport within the channel and sufficiently to block nerve function. Aliphatic alcohols are examples of anesthetics believed to act through physicochemical effects.

Local anesthetic agents having nerve blocking effects have been differentiated between those which produce total blocking of nerve impulse conduction at any impulse frequency (Condouris et al., JADSA, Vol. VIII Number 3, March 1961; Condouris, Epilepsia, 10 (1969) pp. 224–227; Condouris, Advances in Pain Research and Therapy, Vol. 1, pp. 663–667 (1976) ) and those which produce block of a single impulse without blocking high frequency impulses (Condouris et al., The Pharmacologist, Vol. 9, No. 2-Fall, 1967; Condouris et al., Fourth International Congress on Pharmacology, Basel, Switzerland, July 14–18, 1969).

Compounds which will produce a clearly differentiated high frequency impulse block without also significantly affecting single impulse conduction at the same concentration levels are needed in order to provide a better understanding of the mechanism of nerve impulse propagation. It has now been found that certain triazinone derivatives can differentiate between a single impulse and high frequency impulses. Such agents are expected to have clinical utility in situations involving pathological disorders which are characterized by unusual prolonged high frequency discharge and compounds having such activity are useful tools for studying the initiation and propagation of nerve impulses and may be useful as aids in diagnosing and locating diseases characterized by defective nerve conduction. Effector organ response is associated with nerve impulses initiated at a local region of nerve membrane and conducted along an axon to or from the effector organ. Treatments of the type disclosed herein can be used to modify sensations dependent on high frequency impulse trains and may be used to modify conditions caused by high frequency nerve impulse conduction of propagation as an aberrant function such as the nerve impulses associated with low back pain, trigeminal neuralgia, musculo-skeletal pains, dental pain, pain associated with myofacial trigger areas, and similar disorders. Accordingly, it is an object of this invention to provide a method for treating patients suffering from pathological symptoms associated with exaggerated nerve membrane excitation and further, to provide a useful tool for the study and understanding of the propagation of nerve impulses.

SUMMARY OF THE INVENTION

In accordance with this invention, there is provided a method of blocking high frequency nerve impulse conduction by contacting the nerve membrane with a 1,4-disubstituted-1,2-dihydro-1,3,5-triazin-2-one.

DETAILED DESCRIPTION OF THE INVENTION

In accordance with the present invention, a pharmaceutically useful class of 2-triazine derivatives has been found to possess unique effects on nerve impulse conduction. In particular, certain 2-triazinone derivatives have been found to be capable of producing a differentiated nerve conduction response to single impulse and high frequency electrical stimulation. Thus, a particular group of novel 2-triazinone derivatives have been shown to produce substantially complete blocking of axonal conduction initiated by high frequency electrical stimulation while permitting substantially complete conduction of nerve impulse produced by a single electrical stimulus. Accordingly, these compounds are useful in those clinical situations where excitable nerve membrane is spontaneously activated at high frequencies. Under such situations, this particular group of novel triazine derivatives can be utilized to limit the high frequency impulses without limiting the original impulse. Thus, in one of its broad aspects, this invention pertains to the use of triazinones of Formula I below in a method for treating conditions caused by conduction of nerve impulse trains at exaggerated rates by administering an amount of a compound of formula I sufficient to block high frequency nerve impulse conduction.

In a more specific aspect, the invention pertains to a method of treating physiological disorders associated with high frequency discharge of nerve fiber and related physiological disorders caused wherever high frequency discharge of nerve fiber is an aberrant function. Thus, these compounds may be used to relieve or eliminate pain sensation for example, persistant pain such as low back pain, skeletal muscle spasms and the like. They can be used for filtering down to a resting state any exaggerated nerve impulse propagation. They may be useful, for example, in the treatment of trigeminal neuralgia.

In another specific aspect of the invention the triazinones can be used to change the action of effector organs responding to stimulus of high frequency nerve impulse conduction or to change the sensations, particularly aberrant sensations transmitted by high frequency nerve impulses from effector organs.

In still another specific aspect, the compounds of Formula I are useful in determining the role of nerve conduction in the diagnosis and treatment of diseases in which actions or sensations are associated with aberrant high frequency nerve impulse conduction. In view of the unique pharmacological effect of these compounds, they also provide an effective tool for use in the study and understanding of nerve impulse conduction, muscle fiber excitation, and neuromuscular transmission.

The compounds which have been found to be particularly useful for their ability to block high frequency impulse stimulation are compounds of the general formula:

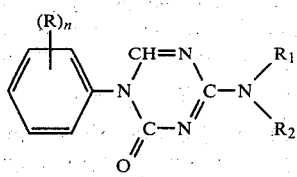

Formula I wherein $R_1$ and $R_2$ are each lower alkyl, aralkyl, hydroxy lower alkyl or lower alkoxy; R is each separately lower alkyl of 1 to 6 carbon atoms, halo; lower alkenyl, lower alkoxy or hydroxy lower alkyl; and n is 1–3.

The more preferred compounds of this invention are described by Formula II:

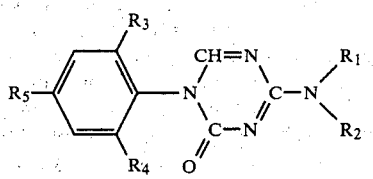

Formula II wherein $R_1$ and $R_2$ are each lower alkyl, hydrogen, aralkyl, hydroxy lower alkyl or lower alkoxy; $R_3$ and $R_4$ are each separately lower alkyl of 1 to 6 carbon atoms or halo and $R_5$ is hydrogen, halo, lower alkyl, lower alkenyl, lower alkoxy or hydroxy lower alkyl; with the proviso that the total number of carbon atoms in $R_1$, $R_2$, $R_3$ and $R_4$ taken together is at least four and no more than about 20 and preferably between 4 and 12; together with the pharmaceutically acceptable salts.

Pharmaceutically acceptable salts of the compounds include acid addition salts and quarternary salts. The compounds can be obtained as acid addition salts prepared from the corresponding free base by recrystallizing from a solution of a non-toxic pharmaceutically acceptable organic or inorganic acid including strong Lewis acids. Other salts, for example, quarternary salts, are prepared by known methods for quarternizing organic nitrogen compounds. The non-toxic acid addition salts that can be conveniently prepared from the novel triazine derivatives of this invention are preferably those prepared from strong acids of low volatility. Among the suitable acids that can be named are the following: Hydrochloric acid, hydrobromic acid, sulfuric acid, nitric acid, phosphoric acid, methane sulfonic acid, benzene sulfonic acid, toluene sulfonic acid, etc.

As used herein, the term "lower alkyl" means a saturated or branched chain hydrocarbon containing from 2 to 6 carbon atoms such as methyl, ethyl, propyl, isopropyl, butyl, secondary butyl, tertiary butyl, isopentyl and the like.

The term "lower alkenyl" is intended to mean lower alkyl groups having at least one double bond.

The term "aralkyl" is intended to mean a lower alkyl group having one or more hydrogen atoms replaced by a phenol group such as, for example, benzyl, phenethyl and the like.

The preferred compounds of Formula I are those wherein $R_3$ and $R_4$ are both lower alkyl and are the same.

A more preferred group is that wherein $R_3$ and $R_4$ are both lower alkyl and are the same, and $R_1$ is hydrogen.

A still more preferred group is that wherein $R_3$ and $R_4$ are both lower alkyl and are the same; $R_1$ is hydrogen, $R_2$ is lower alkyl or hydroxy lower alkyl and $R_5$ is hydrogen.

As exemplary compounds answering to Formula I above, and which are suited for use in the methods of this invention, there can be named the following:

1-(2'6'-diethylphenyl)-4-ethylamino-1,2-dihydro-1,3,5-triazin-2-one 1-(2'6'-diethylphenyl)-4-ethylamino-1,2-dihydro-1,3,5-triazin-2-one hydrochloride 1-(2'6'-diethylphenyl)-4-ethylamino-1,2-dihydro-1,3,5-triazin-2-one methanesulfonate 1-(2'6'-diethylphenyl)-4-ethylamino-1,2-dihydro-1,3,5-triazin-2-one hydrobromide 1-(2'6'-diethylphenyl)-4-ethylamino-1,2-dihydro-1,3,5-triazin-2-one benzenesulfonate 1-(2'6'diethyl-4'-chlorophenyl)-4-ethylamino-1,2-dihydro-1,3,5-triazin-2-one 1-(2'6'-diethyl-4'-bromophenyl)-4-ethylamino-1,2-dihydro-1,3,5-triazin-2-one 1-(2'6'-diethyl-4'-trifluoromethyl)-4-ethylamino-1,2-dihydro-1,3,5-triazin-2-one 1-(2'6'-diethyl-4'-fluorophenyl)-4-ethylamino-1,2-dihydro-1,3,5-triazin-2-one 1-(2'6'-diethyl-4'-ethylenylphenyl)-4-ethylamino-1,2-dihydro-1,3,5-triazin-2-one 1-(2'6'-diethyl-4'-ethoxyphenyl)-4-ethylamino-1,2-dihydro-1,3,5-triazin-2-one 1-(2'6'-diethyl-4'-butoxyphenyl)-4-ethylamino-1,2-dihydro-1,3,5-triazin-2-one 1-[2'6'-diethyl-4'-(2-hydroxyethyl)-phenyl]-4-ethylamino-1,2-dihydro-1,3,5-triazin-2-one 1-(2'4'6'-tributylphenyl)-4-ethylamino-1,2-dihydro-1,3,5-triazin-2-one 1-(2'6'-diethylphenyl)-4-(N,N-dimethylamino) -1,2-dihydro-1,3,5-triazin-2-one 1-(2'6'-diethylphenyl)-4-(N,N-diethylamino)-1,2-dihydro-1,3,5-triazin-2-one 1-(2'6'-diethylphenyl)-4-(butylamino)-1,2-dihydro-1,3,5-triazin-2-one 1-(2'6'-diethylphenyl)-4-(hexylamino)-1,2-dihydro-1,3,5-triazin-2-one 1-(2'6'-diethylphenyl)-4-(sec-butylamino)-1,2-dihydro-1,3,5-triazin-2-one 1-(2'6'-diethylphenyl)-4-(tert-butylamino)-1,2-dihydro-1,3,5-triazin-2-one 1-(2'6'-diethylphenyl)-4-(benzylamino)-1,2-dihydro-1,3,5-triazin-2-one 1-(2'6'-diethylphenyl)-4-(N,N-dibenzylamino)-1,2-dihydro-1,3,5-triazin-2-one 1-(2'6'-diethylphenyl)-4-(N-methyl-N-benzylamino)-1,2-dihydro-1,3,5-triazin-2-one 1-(2'6'-diethylphenyl)-4-(N,N-dimethoxyamino)-1,2-dihydro-1,3,5-triazin-2-one 1-(2'6'-diethylphenyl)-4-(N,N-dibutoxyamino)-1,2-dihydro-1,3,5-triazin-2-one 1-(2'6'-diethylphenyl)-4-(N-methyl-N-methoxyamino)-1,2-dihydro-1,3,5-triazin-2-one 1-(2'6'-diethylphenyl)-4-(N,N-dihydroxymethylamino)-1,2-dihydro-1,3,5-triazin-2-one 1-(2'6'-diethylphenyl)-4-(N-benzyl-N-methoxyamino)-1,2-dihydro-1,3,5-triazin-2-one 1-(2'6'-diethylphenyl)-4-N,N-di-(2-hydroxyethyl)-amino-1,2-dihydro-1,3,5-triazin-2-one
1-(2'6'-diethylphenyl)-4-(N-methyl-N-hydroxymethylamino)-1,2-dihydro-1,3,5-triazin-2-one
1-(2'6'-diethylphenyl)-4-(N-benzyl-N-hydroxymethylamino)-1,2-dihydro-1,3,5-triazin-2-one
1-(2'4'6'-triethylphenyl)-4-methylamino-1,2-dihydro-1,3,5-triazin-2-one
1-(2'4'6'-tripropylphenyl)-4-methylamino-1,2-dihydro-1,3,5-triazin-2-one
1-(2'4'6'-tributylphenyl)-4-methylamino-1,2-dihydro-1,3,5-triazin-2-one
1-(2'4'6'-tri(tert-butylphenyl)-4-methylamino-1,2-dihydro-1,3,5-triazin-2-one
1-(2'4'6'-tripentylphenyl)-4-methylamino-1,2-dihydro-1,3,5-triazin-2-one
1-(2'6'-diethyl-4'-chlorophenyl)-4-methylamino-1,2-dihydro-1,3,5-triazin-2-one
1-(2'6'-diethyl-4'-bromophenyl)-4-methylamino-1,2-dihydro-1,3,5-triazin-2-one
1-(2'6'-diethyl-4'-(sec-butylphenyl)-4-methylamino-1,2-dihydro-1,3,5-triazin-2-one
1-(2'4'6'-triethylphenyl)-4-(N,N,-dimethyl)-4-methylamino-1,2-dihydro-1,3,5-triazin-2-one
1-(2'4'6'-triethylphenyl)-4-(N,N-dibenzyl)-1,2-dihydro-1,3,5-triazin-2-one
1-(2'6'-diethylphenyl)-4-methylamino-1,2-dihydro-1,3,5-triazin-2-one
1-(2'6'-dimethylphenyl)-4-ethylamino-1,2-dihydro-1,3,5-triazin-2-one hydrochloride
1-(2'6'-dimethylphenyl)-4-ethylamino-1,2-dihydro-1,3,5-triazin-2-one methanesulfonate
1-(2'6'-diethylphenyl)-4-methylamino-1,2-dihydro-1,3,5-triazin-2-one hydrochloride
4-dimethylazino-1-(2'6'-dimethylphenyl)-1,2-dihydro-1,3,5-triazin-2-one hydrochloride
1-(2'6'-dimethylphenyl)-4-n-butoxyamino-1,2-dihydro-1,3,5-triazin-2-one
1-(2'6'-dimethylphenyl)-4-sec-butoxyamino-1,2-dihydro-1,3,5-triazin-2-one
1-(2'4'6-trimethylphenyl)-4-ethylamino-1,2-dihydro-1,3,5-triazin-2-one
1-(2'6'-diethylphenyl)-4-2,2,2-trifluoroethylamino)-1,2-dihydro-1,3,5-triazin-2-one
1-(2'6'-dimethylphenyl)-4-ethyoxyamino-1,2-dihydro-1,3,5-triazin-2-one
1-(2'6'-diethylphenyl)-4-propylamino-1,2-dihydro-1,3,5-triazin-2-one
1-(2'6'-diethylphenyl)-4-i-propylamino-1,2-dihydro-1,3,5-triazin-2-one
1-(2'6'-diethylphenyl)-4-(2-hydroxyethyl)amino-1,2-dihydro-1,3,5-triazin-2-one
1-(2'6'-diethylphenyl)-4-cyclopropylamino-1,2-dihydro-1,3,5-triazin-2-one
1-(2'6'-diethylphenyl)-4-benzyl)-1,2-dihydro-1,3,5-triazin-2-one
1-(2'-methyl-6'-ethyl-phenyl)-4-methylamino-1,2-dihydro-1,3,5-triazin-2-one
1-(2'-methyl-6'-ethyl-phenyl)-4-(N,N-dimethylamino)-1,2-dihydro-1,3,5-triazin-2-one
1-(2'-methyl-6'-chlorophenyl)-4-propylamino-1,2-dihydro-1,3,5-triazin-2-one
1-(2'-methyl-6'-ethylphenyl)-4-ethylamino-1,2-dihydro-1,3,5-triazin-2-one
1-(2'6'-dimethyl-4'-hydroxymethyl)-4-ethylamino-1,2-dihydro-1,3,5-triazin-2-one
1-(2'6'-dimethylphenyl)-4-butylamino-1,2-dihydro-1,3,5-triazin-2-one Generally, the compounds when used in accordance with the method of this invention, are believed to exert their effect on high frequency nerve impulse conduction by lodging in the nerve membrane, therefore, selective members in the group of compounds encompassed by Formula I may show some local anesthetic effect in addition to blocking of high frequency nerve impulse conduction. Based on comparative studies, it appears that compounds of increased fat solubility are more likely to have increased local anesthetic effects and correspondingly decreased differential high frequency blocking effects. While the structural activity relationships have not been fully defined, it may be of interest that a methyl group on the phenol ring can be replaced by halo or halo alkyl without loss of activity. Similar substitutions of pharmacologically equivalent functional groups are contemplated as falling within the invention.

The preparations of these compounds are described in an application filed simultaneously herewith and assigned to applicants' assignee. Said copending application is entitled "Triazinones" and the applicants are Douglas, Studt, Won, and Dodson Ser. No. 959,611, 11/13/78, now U.S. Pat. No. 4,246,409. For a more complete description of the triazine derivatives, their synthesis and properties, reference may be had to such copending application, the disclosure of which is incorporated herein by reference.

The test method used to examine the unique local anesthetic activity of the triazine compounds in accordance with this invention involves direct application to the isolated desheathed sciatic-peroneal-tibial trunk of the bullfrog. The methodology used is as follows:

All drug solutions were applied to 15 mm segments of desheathed trunks situated between stimulating and recording electrodes employing a standard pharmacologic technique for observing the conduction blocking effects of local anesthetics.

Briefly summarized, the technique allows nerve impulses to be initiated by means of an electrical stimulus applied to a drug-free segment of a trunk and to be conducted through the treated segment. Recording electrodes placed on the distal side of the treated segment detect only those impulses that were conducted through the 15 mm segment. By relating the amplitude of the recorded compound spike potential to that recorded before the application of drug treatment, an index is available for the proportion of fibers that could conduct impulses through 15 mm of treated length. This index is referred to as "percent of control spike height" or "percent reduction of spike height" or "percent block of conduction".

The source of the nerves is the bullfrog, *Rana castesoeiana*. During dissection, the nerves are exposed to Ringer solution having the following composition: 110 mM NaCl, 3.0 mM KCL, 1.8 mM $CaCl_2$, 20 mM $NaHCO_3$, 2 mM phosphate buffer. The solution is bubbled with 95% $O_2$, 5% $CO_2$ ato maintain a pH of 7.2±0.05 at room temperature (22°-24° C.).

Preparation of Ringer solution with test substance:

First, a quantity of drug is weighed out which would make a 50 mM solution when dissolved in 5.0 ml of Ringer. The drug is dissolved in 0.4 ml of abolute ethanol by stirring for 10 minutes at high speed on a Genie Vortex apparatus. The solution is then brought to 5.0 ml with standard Ringer solution. The drug solution is then dilluted 10 times with Ringer solution to give a final concentration of 5.0 mM. The final solution is bubbled with 95% $O_2$, 5% $CO_2$ to give a pH of 7.2. The final concentration of ethanol is 0.172 M. Whenever the water solubility of the compounds is too low an appropriate solvent preferably DMSO or ethanol, can be used.

To control for the ethanol in the drug solution, the drug-free Ringer solution used to recover nerves from drug effect was made with the same final concentration of ethanol. This ethanol concentration had no effect on conduction.

The same general procedure was used to prepare a solution of the test drug in an dimethylsulfoxide Ringer solution. The final concentration of dimethylsulfoxide (DMSO) was 0.101 M. DMSO had no effect on conduction.

Representative compounds of Formula I when tested by this method showed the following results:

1-(2'6'-dimethylphenyl)-4-methylamino-1,2-dihydro-1,3,5-triazin-2-one hydrochloride proved to have essentially no conduction blocking action at a concentration of 5 mM, which is the high end of concentrations used on desheathed frog trunks with bonafide local anesthetic agents. In four separate experiments, the average reduction in the A B spike potential was only 10%±1.6 (S.E.M.) after 30 minutes contact with the drug. This feeble effect is contrasted with that of 5 mM of the corresponding amidino urea which caused a mean reduction of 77%±8.3 (N=3) within 10 minutes of contact; and a total block within 20 minutes in 2 of 3 trunks.

This test shows 1-(2'6'-dimethylphenyl)-4-methylamino-1,2-dihydro-1,3,5-triazin-2-one hydrochloride to be devoid of any important local anesthetic activity on bullfrog peripheral nerves of the $A\alpha$ and $A\beta$ classification.

However, notwithstanding the absence of local anesthetic activity of the classical type as demonstrated by the above test and other tests generally employed, the compounds of this invention showed an effect on high frequency impulse transmission. The test employed in showing the differentiated local anesthetic activity between single impulse blocking and blocking of high frequency electrical stimulation and the results with representative compounds of the above formula are given below. The methodology is substantially the same desheathed nerve test as that described above.

In this test 1-(2'6'-diethylphenyl)-4-methylamino-1,2-dihydro-1,3,5-triazin-2-one hydrochloride was found to possess weak conduction blocking properties on isolated bullfrog nerves, but to have a substantial capacity to produce high frequency failure.

At a concentration of 5 mM 1-(2'6'-diethylphenyl)-4-methylamino-1,2-dihydro-1,3,5-triazin-2-one hydrochloride reduces the amplitude of a single compound spike by 19%±2.4 in 30 minutes (N=6). This minimal amount of conduction block with 5 mM of the triazine is to be contrasted with an 82%±13.4 (N=3) block within 3 minutes with the corresponding amidino urea.

This difference is illustrated by a comparison or the effects and time-course of 1-(2'6'-diethylphenyl)-4-methylamidinourea (5 mM) with the corresponding 2-triazinone obtained by DMF/DMA cyclization (5 mM) applied to the left and right trunks from the same animal. The amidinourea at this concentration caused a complete block of conduction within 3 minutes; and the triazinone caused only a minimal block of conduction of single impulses. With continued contact, however, the triazinone products its characteristic high frequency failure (h.f.f.) which developed slowly but continually.

Recovery from h.f.f. effects of the triazinone were fairly rapid as shown by good recovery in 10 minutes and nearly complete recovery in 30 minutes.

Clearly, the triazinone has very weak blocking action, and in relation to the corresponding amidinorea, is virtually inactive in depressing excitability under widely spaced stimuli. This compound, therefore, reflects a dissociation between simple conduction block and high frequency failure.

1-(2'6'-diethylphenyl)-4-methylamino-1,2-dihydro-1,3,5-triazin-2-one hydrochloride was also compared with lidocain in two trunks. By comparing 1-(2'6'-diethylphenyl)-4-methylamino-1,2-dihydro-1,3,5-triazin-2-one hydrochloride with lidocaine on the same trunk, the experiment was biased in favor of the triazinone showing any conduction blocking effect, yet it showed no block of single impulses at 5 mM, whereas lidecaine showed blockage at 0.75 and 1.0 mM, concentrations. Hence, 1-(2'6'-diethylphenyl)-4-methylamino-1,2-dihydro-1,3,5-triazin-2-one hydrochloride is virtually without conduction blocking action; and is almost 1/5 as potent as lidocaine on h.f.f.

Since 1-(2'6'-diethylphenyl)-4-methylamino-1,2-dihydro-1,3,5-triazin-2-one hydrochloride is poorly soluble in Ringer solution, it was dissolved first in either of two solvents, DMSO or ethanol. Nearly all the experiments were done using ethanol as the initial solvent, but the results were obtained using the triazinone with two different solvents in a pair of trunks from the same animal. Ethanol or DMSO were present in their respective concentrations in both the triazinone solutions *and* in the normal, drug-free Ringer solution used in the recovery of the nerves. The results show that neither of the two solvents were responsible for the nerve membrane effects observed.

1-(2'6'-diethylphenyl)-4-methylamino-1,2-dihydro-1,3,5-triazin-2-one hydrochloride is virtually without blocking action in nerves stimulated at a low frequency, i.e., 0.5 Hz, at a concentration of 5 mM. The average reduction in the compound spike of only 20% in 30 minutes stands in marked contrast to the total block within a few minutes by 5 mM 1-(2'6'-diethylphenyl)-3-methylamidinourea, its amidinourea precurser.

1-(2'6'-diethylphenyl-4-methylamino-1,2-dihydro-1,3,5-triazin-2-one hydrochloride has a substantial effect on the membrane recovery processes as evidenced by the development of high frequency failure. This phenomenon is associated with the prolongation of the refractory period of the membrane, which, in turn, limits the nerve in its ability to respond to repetitive stimulation at higher frequencies.

The foregoing tests illustrate the unique ability of these compounds to selectively block high frequency nerve impulses and shows their value as useful tools for pharmacological research in understanding the chemistry involved in the generation, conduction and blocking of nerve impulses and also the causes and treatment of abnormal nerve function in mammalian species. These compounds exert this effect at the nerve membrane level and the effect is completely reversible after withdrawal of the compound. These compounds, when formulated with suitable carrier materials for administration in a manner which allows the drug to reach the nerve membrane at effective dose levels, will block high frequency impulse propagation in the nerve membrane indicating use in clinical situations involving nerve stimulation at exaggerated frequency such as the symptomatic treatment of Parkinson's disease and other disorders characterized by undesired nerve impulse propagation. Moreover, since these compounds do not show any effect on the central nervous system when administered orally, they may find use in the control of tremor without adversely affecting mood. In most cases, the compounds are absorbed when taken orally and exert their effect on nerve membrane of the gastrointestinal tract. The compounds can also be applied directly to the nerve, for example, by injection such as intradermal injection for a local effect.

The compositions of the present invention can be prepared in forms suitable for administration to humans and animals by compounding an effective single dose amount of a compound of Formula I above with known ingredients generally employed in the preparation of therapeutic compositions provided as tablets, capsules, lozenges, chewable lozenges, pills, powder, granules, suspensions, oil-in-water or water-in-oil emulsions, or other similar forms which can be taken orally. Since the compounds are readily absorbed into the blood stream from the stomach and intestines when taken orally, the preferred method of treatment is to give the drug orally which is also the safest and most practical route of administration. Optional methods can be used. Where, for example, the patient cannot swallow or has difficulty in swallowing, other methods of administration which permit the drug to be absorbed from the gastrointestinal tract or which deliver a solution of the drug directly to the blood stream can be employed. Still other methods of administration such as intra-muscular injection or injection directly into myofacial trigger areas and the like can be used.

The dosage regimens in carrying out the pharmacotherapeutic methods utilizing the triazine compositions of this invention are those which insure maximum therapeutic response until improvement is obtained and thereafter the minimum effective level which gives relief. Thus, in general, the dosages are those that are therapeutically effective in blocking transmission of high frequency nerve impulses. In general, the single oral dose will contain between about 100 mg and 2000 mg (preferably in the range of 500 to 1000 mg). Fractional or multiple doses can of course be given bearing in mind that in selecting the appropriate dosage in any specific case, consideration must be given to the patient's weight, general health, age, and other factors which may influence response to the drug. The drug response on oral administration usually follows within 10 to 30 minutes after administration and is maintained for 1 to 4 hours. The drug is generally given in single doses 2 to 4 times daily or as required to maintain an effective drug level in the blood stream for continuous relief of high frequency nerve impulses.

Compositions intended for oral use may be prepared according to methods known generally in the art, such compositions may contain one or more agents selected from the group consisting of sweetening agents, flavoring agents, coloring agents and preserving agents, in order to provide a pharmaceutically elegant and palatable preparation. Orally, they may be administered in tablets, lozenges, aqueous or oily suspensions dispersible powders or granules, emulsions, hard or soft capsules, or syrups or elixers which contain the active triazine ingredient in admixture with non-toxic pharmaceutically acceptable excipients. Excipients which may be, for example, inert diluents, such as calcium carbonate, sodium carbonate, lactose, calcium phosphate or sodium phosphate; granulating and disintegrating agents, for example, starch, gelatin or acacia; and lubricating agents, for example, magnesium stearate, stearic acid or talc. The tablets may be uncoated or they may be coated by known techniques to make them more effective for example, to delay disintegration or absorption or to make them more palatable or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active triazine form a further embodiment of this invention. Excipients suitable for aqueous suspensions, may be employed if desired. These excipients are suspending agents, for example, sodium carboxymethyl-cellulose, methyl-cellulose, hydroxypropyl-methylcellulose, sodium alginate, polyvinylpyrrolidine, gum tragacanth and gum acacia; dispersing or wetting agents may be a naturally occurring phosphatide, for example, lecithin; or condensation products of ethylene oxide with long chain aliphatic alcohols, for example, heptadecaethylencoxy-cetanol; or condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxicant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occuring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweetening and flavoring agents.

Syrups and elixers may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersible or wetting agents and suspending atents which have been mentioned above. The sterile injectable preparation may also be a sterile injectable solution or suspension in a non-toxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Generally, these compounds may be tableted or otherwise formulated for oral use so that for every 100 parts by weight of the composition, there are present between 5 and 95 parts by weight of the active ingredient.

Various tests carried out in animal models show that the triazinones of Formula I above exhibit reactions that can be correlated with activity in humans. The following tests show the ability of these compounds to inhibit nerve impulse transmission in test animals indicative of activity in humans.

The following examples are given by way of illustrating the preparation of the active triazinones used in the method and compositions of this invention. Novel therapeutic compositions are also examplified. It will be understood that variations in amounts and adjuvants used in compounding suitable compositions can be made without departing from the teaching of this invention which is the administration of a 1,4-disubstituted-1,2-dihydro-1,3,5-triazin-2-one of Formula I in a manner and in amounts sufficient to provide and maintain an effective level at the nerve membrane for prophylactic or therapeutic use. If desired, the compounds can be formulated with other active ingredients or administered with other drugs or as part of a program of therapy that includes suppression of high frequency nerve membrane. The salts of compounds of formula I, including acid addition salts and quarternary ammonium salts are particularly suitable for preparing pharmaceutical compositions. The acid addition salts of strong acids such as the hydrochloride, the hydrobromide, sulfate, nitrate, phosphate, methane sulfonate, benzene sulfonate and the like are especially useful. The salts of any strong Lewis acids can be used.

EXAMPLE 1

Preparation of 1-(2'6'-diethylphenyl)-4-methylamino-1,2-dihydro-1,3,5-triazin-2-one About 200 mg. of 1-(2'6'-diethylphenyl)-3-methylamidinourea hydrochloride was introduced in a gas cchromatograph hypo vial and dissolved in 1 ml of acetonitrile. To the solution was added 0.2 ml of di-methylformamide dimethyl acetal (DMF-DMA) reagent. The vial was sealed with crimper and heated at 105° C. for 15 minutes in an oven. Seven vials were made. The contents of the vials were then put into a long-neck round bottom flask and evaporated to dryness by a flask evaporator. The solid mass was dissolved in a mixture of 30 ml of $CHCl_3$ and 20 ml of water and shaken vigorously in a 60 ml separatory funnel. The aqueous layer was discarded and 20 ml of water was added and shaken. The $CHCl_3$ layer was then taken and about 10 g of anhydrous $Na_2SO_4$ was added, the $CHCl_3$ solution was decanted into a flask and evaporated to dryness. The solid material was dissolved in about 80 ml of pentanone-2 and hexane (30:10) at 70° C. The solution was concentrated and crystallized upon cooling. The crystals were collected and dried in a desiccator with $P_2O_5$ with vacuum for one hour.

| Elemental Analysis | MP:210-211° C. | | |
|---|---|---|---|
| | C | H | N |
| Calculated | 65.09 | 7.02 | 21.89 |
| Found | 65.34 | 7.01 | 21.83 |

By analogous procedure utilizing the corresponding amidinourea starting materials, the following compounds are prepared.

1-(2'6'-dimethylphenyl)-4-n-butylamino-1,2-dihydro-1,3,5-triazin-2-one hydrochloride

| MOLECULAR FORMULA: $C_{15}H_{21}ClN_4O$ | | | |
|---|---|---|---|
| | C | H | N | Cl |
| Calculated: | 58.34 | 6.85 | 18.14 | 11.48 |
| Found: | 58.07 | 6.95 | 18.31 | 11.53 |
| Mol. Wt: 308.8 | | | | |
| M.P. 216-218° C. | | | | |

1-(2'6'-diethylphenyl)-4-ethylamino-1,2-dihydro-1,3,5-triazin-2-one hydrochloride

| MOLECULAR FORMULA: $C_{15}H_{21}ClN_4O$ | | | |
|---|---|---|---|
| | C | H | N | Cl |
| Calculated: | 58.34 | 6.86 | 18.14 | 11.48 |
| Found: | 58.63 | 6.93 | 18.29 | 11.59 |
| Mol. Wt: 308.813 | | | | |
| M.P.:199.5-103.5° C. | | | | |

1-(2'6'-diethyphenyl)-4-amino-1,2-dihydro-1,3,5-triazin-2-one

| MOLECULAR FORMULA: $C_{13}H_{16}N_4O$ | | |
|---|---|---|
| | C | H | N |
| Calculated: | 63.92 | 6.60 | 22.93 |
| Found: | 63.88 | 6.77 | 22.78 |
| Mol. Wt: 244.298 | | | |
| M.P. >250° C. | | | |

1-(2'6'-diethylphenyl)-4-n-propylamino-1,2-dihydro-1,3,5-triazin-2-one hydrochloride

| MOLECULAR FORMULA: $C_{16}H_{23}ClN_4O$ | | | |
|---|---|---|---|
| | C | H | N | Cl |
| Calculated: | 59.53 | 7.18 | 17.35 | 10.98 |
| Found: | 59.04 | 7.33 | 17.33 | 11.29 |
| Mol. Wt: 322.840 | | | | |
| M.P.: 166.5-170° C. | | | | |

1-(2'6'-diethylphenyl)-4-n-butylamino-1,2-dihydro-1,3,5-triazin-2-one

| MOLECULAR FORMULA: $C_{17}H_{24}N_4O$ | | | |
|---|---|---|---|
| | C | H | N |
| Calculated: | 67.97 | 8.05 | 18.65 |
| Found: | 68.14 | 8.03 | 18.95 |

Mol. Wt: 300.4
M.P.: 178–179° C.

1-(2'6'-dimethylphenyl)-4-n-propylamino-1,2-dihydro-1,3,5-triazin-2-one

| MOLECULAR FORMULA: $C_{14}H_{18}N_4O$ | | | |
|---|---|---|---|
| | C | H | N |
| Calculated: | 65.10 | 7.02 | 21.69 |
| Found: | 65.21 | 7.03 | 21.59 |

Mol. Wt: 258.325
M.P.: 191.5–193° C.

1-(2'6'-dimethylphenyl)-4-ethylamino-1,2-dihydro-1,3,5-triazin-2-one

| MOLECULAR FORMULA: $C_{13}H_{16}N_4O$ | | | |
|---|---|---|---|
| | C | H | N |
| Calculated: | 63.91 | 6.60 | 22.93 |
| Found: | 63.84 | 6.66 | 23.38 |

Mol. Wt: 244.3
M.P.: 193–194° C.

1-(2'6'-dimethylphenyl)-4-amino-1,2-dihydro,1,3,5-triazin-2-one

| MOLECULAR FORMULA: $C_{11}H_{12}N_4O$ | | | |
|---|---|---|---|
| | C | H | N |
| Calculated: | 61.10 | 5.59 | 25.91 |
| Found: | 60.75 | 5.76 | 25.90 |

Mol. Wt: 216.244
M.P.: 258.5–259° C.

EXAMPLE 2

1-(2'6'-diethylphenyl)-4-methylamino-1,2-dihydro-1,3,5-triazin-2-one hydrochloride To a suspension of 22.8 g (80.0 mmol) of 1-(2,6-diethylphenyl)-3-methylamidinourea in $CH_3CN$ (100 ml) were added 19.1 g (160.0 mmol) of DMF-DMA and the reaction mixture was heated at reflux for 3 hours. The $CH_3CN$ was removed under reduced pressure and the residue partitioned between $CHCl_3$ and $H_2O$. The layers were separated and the aqueous layer extracted with $CHCl_3$ (1×100 ml), dried ($MgSO_4$) and concentrated under reduced pressure to give an off-white solid, which by NMR confirmed the desired free base. The solution was dissolved in $H_2OH$ and acidified with HCl/MeOH and the MeOH removed under reduced pressure to give an off-white solid which was crystallized from $CH_3CN$ to give after vacuum drying the weekend (105° C., house vacuum) 16.7 g (71%) of crude product. The material was recrystallized from $CH_3CN$ (a hot filtration was necessary to remove some undissolved solid) to give 11.0 g (47%) of desired product as a white crystalline solid:

| Analysis calculated for: $C_{14}H_{18}N_4OHCl$ | | | MP: 208–15° C. | |
|---|---|---|---|---|
| | C | H | N | Cl |
| Calculated: | 57.04 | 6.50 | 19.01 | 12.03 |
| Found: | 57.14 | 6.51 | 19.38 | 12.01 |

EXAMPLE 3

4-dimethylamino-1-(2'6'-dimethylphenyl)-1,2-dihydro-1,3,5-triazin-2-one hydrochloride To a suspension of 19.0 g (0.07 mole) of 1-(2,6-dimethylphenyl)-3-(N,N-dimethyl)-amidinourea in acrylonitrile (100 m) were added 16.7 g (0.14 mole) of DMF-DMA and the mixture refluxed for 2 hours. The acrylonitrile was removed under reduced pressure and the residue partitioned between $H_2O$ and $CHCl_3$. The layers were separated and the aqueous layer extracted with $CHCl_3$ (1×100 ml). The $CHCl_3$ extracts were washed with $H_2$) (1×50 ml), dried over $MgSO_4$ and concentrated at reduced pressure to give an oil. Trituration of the oil in EtOH precipitated a white solid which was filtered and washed with EtOH to give the desired product after air drying. The solid was dissolved in McOH and acidified with HCl/McOH The McOH was removed under reduced pressure to give a white solid which was triturated with $CH_3CN$, filtered and washed with $CH_3CN$ to give 7.5 g (38%) of product which by NMR seemed to be a hydrate or wet. The solid was vacuum dried for 6 hours at 100° C. under vacuum.

| Analysis calculated for: $Cl_{13}H_{10}N_4O$ . HCL | | | | |
|---|---|---|---|---|
| | C | H | N | Cl |
| Calculated | 55.61 | 6.10 | 19.96 | 12.63 |
| Found | 55.81 | 5.96 | 20.31 | 12.46 |

EXAMPLE 4

Therapeutic compositions of the invention are prepared by using known techniques for compounding employing either the base or a salt as the active ingredient along with the non-toxic excipients chosen in accordance with the particular form and properties desired for the therapeutic composition.

Tablets which can be advantageously used for either remedial or prophylactic treatments in accordance with this invention, can be supplied in a form which provides relief from symptoms of disorders associated with aberrant nerve impulse conduction when taken at a rate of 4 to 6 tablets per day containing between about 200 to 2000 mg. of the active ingredient. An exemplary formulation which can be utilized is, for example, the following:

| | |
|---|---|
| 1-(2'6'-diethylphenyl)-4-methylamino-1,2-dihydro-1,3,5-triazin-2-one | 500 mg. |
| tricalcium phosphate | 200 mg. |
| talc | 50 mg. |
| magnesium stearate | 10 mg. |
| polyvinyl acetate | 40 mg. |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 850 mg.

EXAMPLE 5

A lot of 1,000 tablets each containing 1 g of 1-(2'6'-diethylphenyl)-4-methylamine-1,2-dihydro-1,3,5-triazin-2-one is prepared from the following types and amounts of ingredients:

| | |
|---|---|
| 1-(2'6'-diethylphenyl)-4-methylamino 1,2-dihydro-1,3,5-triazin-2-one | 1 kg. |
| dicalcium phosphate | 1 kg. |
| methylcellulose USP | 75 g. |
| talc | 150 g. |
| cornstarch | 200 g. |
| magnesium stearate | 10 g. |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 6

A lot of 2-piece hard gelatin capsules, each containing 500 mg. of 1-(2'6'-dimethylphenyl)-4-ethylamino-1,2-dihydro-1,3,5-triazin-2-one are prepared from the following types and amounts of ingredients (the amounts given are per capsule).

| | |
|---|---|
| 1-(2'6'-dimethylphenyl)-4-ethylamino-1,2-dihydro-1,3,5-triazin-2-one | 500 g. |
| dicalcium phosphate | 500 g. |
| talc | 150 g. |
| magnesium stearate | 5 g. |

The ingredients are mixed thoroughly and filled into capsules which are used for oral administration at the rate of about one every four hours. If desired, slow release forms can be provided or delay release forms depending on choice of capsules and formulating ingredients.

EXAMPLE 7

A sterile solution suitable for intramuscular or interperitioneal injection, and containing 10 mg. of 1-(2'6'-dimethylphenyl 4 methylamino-1,2-dihydro-1,3,5-triazin-2-one hydrochloride in each, 10 ml. (1:1 wt/volume), is prepared from the following ingredients:

| | |
|---|---|
| 1-(2'6'-dimethylphenyl)-4-ethylamino-1,2-dihydro-1,3,5-triazin-2-one hydrochloride | 10 g. |
| benzyl benzoate | 100 ml. |
| methylparaben | 1 g. |
| propylparaben | 0.5 g. |
| cottonseed oil g.s. | 500 ml. |

EXAMPLE 8

Ten thousand tablets for oral use, each containing 50 mg. of 1-(2'6'-diethylphenyl-4-methylamino-1,2-dihydro-1,3,5-triazin-2-one, are prepared from the following types and amounts of material:

| | |
|---|---|
| 1-(2'6'-diethylphenyl)-4-methylamino-1,2-dihydro-1,3,5-triazin-2-one | 500 g. |
| Lactose U.S.P. | 350 g. |
| Potato Starch U.S.P. | 346 g. |

The mixture is moistened with an alcoholic solution of 20 g. of stearic acid and granulated through a sieve. After drying, the following ingredients are added:

| | |
|---|---|
| Potato Starch U.S.P. | 320 g. |
| Talc | 400 g. |
| Magnesium stearate | 500 g. |
| Colloidal silicium dioxide | 64 g. |

The mixture is thoroughly mixed and compresseed into tablets.

EXAMPLE 9 five hundred ampoules each with 2 ml. of solution which contain 15 mg. of 1-(2'6'-dimethylphenyl)-4-ethylamino-1,2-dihydro-1,3,5-triazin-2-one is prepared from the following types and amounts of materials:

| | |
|---|---|
| 1-(2'6'-dimethylphenyl)-4-ethylamino-1,2-dihydro-1,3,5-triazin-2-one | 7.5 g. |
| Ascorbic acid | 1 g. |
| sodium bisulphite | 0.5 g. |
| sodium sulphite | 1 g. |

EXAMPLE 10

Capsules are prepared as follows:
15 g. of 1-(2'6'-diethylphenyl)-4-methylamino-1,2-dihydro-1,3,5-triazin-2-one,
3 g. magnesium stearate,
2 g. of finely divided silica sold under the trademark CAB-O-SIL by Godfrey L. Cabot, Inc., Bosten, MA, and,
369 g. of lactose.
The ingredients are thoroughly mixed with each other and the mixture is filled in gelatin capsules. Each capsule contains 500 mg. of the composition and thus, 15 mg. of 1-(2'6'-diethylphenyl)-4-methylamino-1,2-dihydro-1,3,5-triazin-2-one.

EXAMPLE 11

50 g. of 1-(2'6'-diethylphenyl)-4-methylamino-1,2-dihydro-1,3,5-triazin-2-one, 5 g. of propyl p-hydroxybenzoate are dissolved and dilluted to 5000 cc. with twice distilled water after the addition of modified Sorensen buffer solution in an amount sufficient to adjust the pH-value to a pH of 6.0. Sodium chloride is dissolved therein in an amount sufficient to render the resulting solution isotonic. The final solution, through a bacteriological filter and the filtrate is autoclaved at 120° C. for 15 minutes to yield a parenterally applicable solution which contains 50 mg. of 1-(2'6'-diethylphenyl)-4-methylamino-1,3,5-triazin-2-one in 5 cc.

We claims:
1. A method which comprises selectively blocking the conduction of high frequency nerve impulses without substantially affecting the transmission of single impulse nerve conduction by exposing living nerve fiber to an effective amount of a compound of the formula

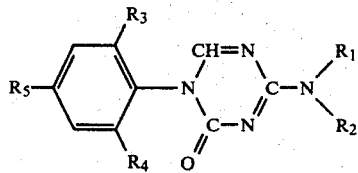

wherein $R_1$ and $R_2$ are each lower alkyl, hydrogen, aralkyl, hydroxy lower alkyl or lower alkoxy; $R_3$ and $R_4$ are each separately lower alkyl of 1 to 6 carbon atoms or halo and $R_5$ is hydrogen, halo, lower alkyl, lower alkenyl, lower alkoxy or hydroxy lower alkyl; with the proviso that the total number of carbon atoms in $R_1$, $R_2$, $R_3$ and $R_4$ taken together is at least four and no more than about 20; together with the pharmaceutically acceptable salts thereof.

2. A method according to claim 1 wherein a living nerve fiber of a mammalian species is contacted with an effective amount of said compound in vivo.

3. A method according to claim 1 wherein a living nerve fiber is contacted with said compound in vitro.

4. A method for treating physiological disorders in mammalian species characterized by aberrant high frequency discharge of nerve fiber which comprises modifying the nerve impulse conductivity by administering to a patient in need of such therapy an effective amount of a compound of the formula:

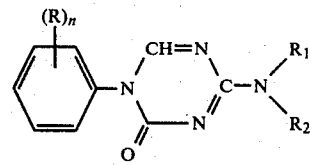

wherein $R_1$ and $R_2$ are each lower alkyl, aralkyl, hydroxy lower alkyl of lower alkoxy; R is each separately lower alkyl of 1 to 6 carbon atoms, halo, lower alkenyl, lower alkoxy or hydroxy lower alkyl; and n is 1–3; together with the pharmaceutically acceptable salts thereof.

* * * * *

UNITED STATES PATENT AND TRADEMARK OFFICE
CERTIFICATE OF CORRECTION

PATENT NO. : 4,298,608
DATED : November 3, 1981
INVENTOR(S) : George A. Condouris et al It is certified that error appears in the above—identified patent and that said Letters Patent is hereby corrected as shown below:

Col. 12, line 44       "103.5°" should read --203.5°--.

Col. 14, line 28       "McOH" should read --MeOH--.

Col. 16, line 40       "Bosten" should read --Boston--.

Signed and Sealed this

Twenty-third Day of March 1982

|SEAL|

Attest:

Attesting Officer

GERALD J. MOSSINGHOFF

Commissioner of Patents and Trademarks